United States Patent
Nielsen

(10) Patent No.: US 10,744,056 B2
(45) Date of Patent: *Aug. 18, 2020

(54) APPARATUS FOR TREATING INFLAMMATORY SYMPTOMS ASSOCIATED WITH PLANTAR FASCIITIS

(71) Applicant: ThermaWedge Enterprises, Inc., Richmond (CA)

(72) Inventor: Susan V. Nielsen, Richmond (CA)

(73) Assignee: ThermaWedge Enterprises, Inc., Richmond (CA)

( * ) Notice: Subject to any disclaimer, the term of this patent is extended or adjusted under 35 U.S.C. 154(b) by 110 days.

This patent is subject to a terminal disclaimer.

(21) Appl. No.: 16/165,921

(22) Filed: Oct. 19, 2018

(65) Prior Publication Data

US 2019/0117492 A1    Apr. 25, 2019

Related U.S. Application Data

(63) Continuation of application No. 15/896,663, filed on Feb. 14, 2018, now Pat. No. 10,219,967, which is a
(Continued)

(51) Int. Cl.
*A61H 1/02* (2006.01)
*A61H 15/00* (2006.01)
(Continued)

(52) U.S. Cl.
CPC ............. *A61H 1/0266* (2013.01); *A61F 7/10* (2013.01); *A61H 15/00* (2013.01); *A63B 23/00* (2013.01);
(Continued)

(58) Field of Classification Search
CPC ........ A63B 21/00047; A63B 21/00058; A63B 21/00061; A63B 21/00065;
(Continued)

(56) References Cited

U.S. PATENT DOCUMENTS 3,972,322 A    8/1976  Finn
4,693,470 A    9/1987  Ogawa
(Continued)

FOREIGN PATENT DOCUMENTS

CN    202314287    7/2012
WO   2004058132    7/2004
(Continued)

OTHER PUBLICATIONS

USPTO; Non-Final Office Action dated Aug. 18, 2017 in U.S. Appl. No. 15/034,381.
(Continued)

*Primary Examiner* — Gary D Urbiel Goldner
(74) *Attorney, Agent, or Firm* — Snell & Wilmer L.L.P.

(57) ABSTRACT

The present invention relates to an apparatus for treating inflammatory symptoms associated with plantar fasciitis in a foot. The apparatus comprises an inclined ramp surface, a flat surface adjacent to the inclined ramp surface, a dowel rollable along both the inclined ramp surface and the flat surface, and a pocket coupled to the flat surface, wherein the pocket is disposed radially outward from the flat surface and ascending the inclined ramp. The apparatus may further comprise a gel pack retained in the pocket, which may be configured for cooling at least one portion of a sole of the foot.

12 Claims, 4 Drawing Sheets

Related U.S. Application Data continuation of application No. 15/034,381, filed as application No. PCT/CA2014/000761 on Oct. 24, 2014, now Pat. No. 9,931,264.

(60) Provisional application No. 61/903,702, filed on Nov. 13, 2013.

(51) Int. Cl.
*A61F 7/10* (2006.01)
*A63B 23/00* (2006.01)
*A61F 7/00* (2006.01)

(52) U.S. Cl.
CPC . *A61F 2007/0047* (2013.01); *A61F 2007/108* (2013.01); *A61H 2015/0014* (2013.01); *A61H 2201/0207* (2013.01); *A61H 2201/0214* (2013.01); *A61H 2201/0257* (2013.01); *A61H 2201/1284* (2013.01); *A63B 2023/006* (2013.01)

(58) Field of Classification Search
CPC ........ A63B 21/00069; A63B 21/00072; A63B 21/00076; A63B 21/00178; A63B 21/00181; A63B 21/00185; A63B 21/002; A63B 21/0023; A63B 21/012; A63B 21/0125; A63B 21/015; A63B 21/06; A63B 21/0615; A63B 21/0616; A63B 21/0617; A63B 21/065; A63B 21/068; A63B 21/08; A63B 21/15; A63B 21/159; A63B 21/22; A63B 21/4015; A63B 21/4023; A63B 21/4025; A63B 21/4027; A63B 21/4029; A63B 21/4031; A63B 21/4033; A63B 21/4035; A63B 21/4037; A63B 21/4039; A63B 21/4045; A63B 21/4047; A63B 21/4049; A63B 22/20; A63B 22/201; A63B 2023/006; A63B 23/04; A63B 23/0494; A63B 23/08; A63B 23/085; A63B 23/10; A63B 69/0057; A63B 69/0059; A63B 2069/0062; A63B 71/0054; A63B 2071/0063; A63B 2071/0072; A63B 2208/02; A63B 2208/0209; A63B 2208/0228; A63B 2208/0233; A63B 2210/50; A63B 2210/58; A63B 2213/00; A63B 2225/09; A63B 2225/093; A63B 2225/66
See application file for complete search history.

(56) References Cited

U.S. PATENT DOCUMENTS

| | | |
|---|---|---|
| 5,056,507 A | 10/1991 | Yum |
| 5,087,036 A | 2/1992 | Cooper |
| 5,752,330 A | 5/1998 | Snabb |
| 5,891,002 A | 4/1999 | Maki |
| 6,074,414 A | 6/2000 | Haas et al. |
| 6,110,078 A | 8/2000 | Dyer |
| 6,244,992 B1 | 6/2001 | James |
| 6,589,141 B1 | 7/2003 | Flaggs |
| 6,602,212 B1 | 8/2003 | Ahn |
| 6,984,197 B2 | 1/2006 | Sugiyama et al. |
| 7,300,026 B2 | 11/2007 | Pap |
| 7,399,285 B2 | 7/2008 | Stein |
| 8,241,232 B2 | 8/2012 | Sanders |
| 8,360,940 B2 | 1/2013 | Kole et al. |
| 8,475,397 B2 | 7/2013 | Ching-Hua et al. |
| 9,931,264 B2 | 4/2018 | Nielsen |
| 10,219,967 B2 | 3/2019 | Nielsen |
| 2004/0023764 A1 | 2/2004 | Repking |
| 2004/0082886 A1 | 4/2004 | Timpson |
| 2004/0215123 A1 | 10/2004 | Slautterback et al. |
| 2005/0131324 A1 | 6/2005 | Bledsoe |
| 2005/0228332 A1 | 10/2005 | Bushby |
| 2007/0260164 A1 | 11/2007 | Chiodo et al. |
| 2009/0024066 A1 | 1/2009 | Sorg |
| 2009/0062699 A1 | 3/2009 | Yang |
| 2010/0036296 A1 | 2/2010 | Sancho Serrats |
| 2011/0054368 A1 | 3/2011 | Sanders |
| 2011/0183815 A1 | 7/2011 | Janzen |
| 2011/0295167 A1 | 12/2011 | Suttman |
| 2012/0172958 A1 | 7/2012 | Snyder |
| 2013/0035217 A1 | 2/2013 | Beck et al. |
| 2013/0218061 A1 | 8/2013 | Cowan |
| 2014/0057765 A1 | 2/2014 | Dalton |
| 2014/0100086 A1 | 4/2014 | Pagliaro |
| 2014/0107554 A1 | 4/2014 | Bushby |
| 2014/0256525 A1 | 9/2014 | Mueller |
| 2016/0270998 A1 | 9/2016 | Nielsen |
| 2018/0168906 A1 | 6/2018 | Nielsen |

FOREIGN PATENT DOCUMENTS

| | | |
|---|---|---|
| WO | 2010131038 | 1/2011 |
| WO | 2015070315 | 5/2015 |

OTHER PUBLICATIONS

USPTO; Notice of Allowance dated Jan. 25, 2018 in U.S. Appl. No. 15/034,381.
USPTO; Non-Final Office Action dated Mar. 29, 2018 in U.S. Appl. No. 15/896,663.
USPTO; Notice of Allowance dated Aug. 16, 2018 in U.S. Appl. No. 15/896,663.
PCT; International Search Report dated Feb. 12, 2015 in International Application No. PCT/CA2014/000761.
PCT; Written Opinion dated Feb. 12, 2015 in International Application No. PCT/CA2014/000761.
PCT; International Preliminary Report on Patentability dated May 17, 2016 in International Application No. PCT/CA2014/000761.
http://www.ftter1.com/Fitterfirst-Slant-Board_p_169.html, Fitterfirst Slant Board Website printout, 14 pages.
http://www.jwedge.com/, Jwedge Website printout, 3 pages.
Http://www.orthosleeve.com/shop/foot-gym-foot-exercises/, Orthosleeve Website printout, 18 pages.
Singh et al., "Fortnightly Review, Plantar Fasciitis," British Medical Journal, vol. 315(7101), pp. 172-175, (Jul. 1997).

APPARATUS FOR TREATING INFLAMMATORY SYMPTOMS ASSOCIATED WITH PLANTAR FASCIITIS

CROSS REFERENCE TO RELATED APPLICATIONS

This application is a continuation of U.S. patent application Ser. No. 15/896,663 filed Feb. 14, 2018, entitled "METHODS FOR TREATING INFLAMMATORY SYMPTOMS ASSOCIATED WITH PLANTAR FASCIITIS, which is a continuation of U.S. patent application Ser. No. 15/034,381, filed May 4, 2016 which is now an issued U.S. Pat. No. 9,931,264, entitled "APPARATUS FOR TREATING INFLAMMATORY SYMPTOMS ASSOCIATED WITH PLANTAR FASCIITIS," which is a U.S. National Stage patent application of PCT Patent Application No. PCT/CA2014/000761, filed Oct. 24, 2014, entitled "METHODS FOR TREATING INFLAMMATORY SYMPTOMS ASSOCIATED WITH PLANTAR FASCIITIS," which claims priority to U.S. Provisional Patent Application Ser. No. 61/903,702, filed Nov. 13, 2013, entitled "METHODS FOR TREATING INFLAMMATORY SYMPTOMS ASSOCIATED WITH PLANTAR FASCIITIS," which are incorporated herein by reference in their entirety.

BACKGROUND

Field of Invention

The present invention relates to a method for treating inflammatory symptoms associated with plantar fasciitis in a foot, as well as an apparatus for carrying out such method. More particularly, the method involves stretching gastrocnemius and soleus muscles associated with the foot and simultaneously cooling at least one portion of the sole of the foot.

Description of Related Art

Plantar fasciitis is an inflammatory condition involving the connective tissue of the sole of a human foot. Overstressing this connective tissue can lead to inflammation and an afflicted individual will commonly suffer from mild to severe heel pain. If left untreated, plantar fasciitis can severely impact an individual's walking and other daily activities.

Plantar fasciitis is a very prevalent inflammatory condition. According to the American Academy of Orthopaedic Surgeons, approximately 2 million Americans are treated for plantar fasciitis each year; the costs associated with treating plantar fasciitis run into the hundreds of millions of dollars on an annual basis (see, for e.g.: Singh et al. BMJ 315(7101): 172-175). Despite the significant prevalence of this inflammatory condition, there are limited options available for successfully treating plantar fasciitis and the inflammatory symptoms related thereto.

For example, U.S. Pat. No. 8,241,232, which issued to Sanders, describes a foot pain relief device that contains a toe strap. The toe strap is fastened around the ankle and the toes to attempt to flex the toes upward. A second strap, referred to in the '232 patent as a ball strap, can be coupled with the toe strap and a ball, threaded to such ball strap, can be used to provide directed pressure on a component of the plantar fascia.

U.S. Pat. No. 6,110,078, which issued to Dyer, describes a passive stretching device consisting primarily of two hinged plates with a variably tensioning mechanism. Applied to the foot and lower leg, the device purports to provide a progressive stretch of the plantar fascia, Achilles tendon and related muscles.

Other known treatments for plantar fasciitis include the use of steroid-containing compositions (see, for e.g., WO2010131038, which was applied for by Hulley et al.). Additionally, other known treatments for these plantar fasciitis-related symptoms include the use of non-steroidal anti-inflammatory drugs, the use of modified footwear, for example by using custom foot orthotics, and, in some instances, invasive surgery.

Accordingly, there remains a need for devices and methods that can efficiently and effectively treat plantar fasciitis, and the inflammatory symptoms related thereto.

SUMMARY OF INVENTION

In one aspect, a method for treating inflammatory symptoms associated with plantar fasciitis in a foot is disclosed. The method involves stretching gastrocnemius and soleus muscles associated with the foot by placing the sole of the foot on an inclined ramp surface, and cooling at least one portion of the sole of the foot.

The method may further involve providing localized pressure to at least one portion of the plantar fascia. The method may also further involve providing localized pressure to a portion of the foot below the toes, to cause dorsiflexion thereof.

The method may involve at least two of the foregoing steps being carried out simultaneously. Further, the method may further involve at least three of the foregoing steps being carried out simultaneously.

In another aspect, an apparatus for treating inflammatory symptoms associated with plantar fasciitis in a foot is disclosed. The apparatus includes an inclined ramp surface for stretching gastrocnemius and soleus muscles associated with the foot, and cooling means engageable with the inclined ramp surface for cooling at least one portion of the sole of the foot while the gastrocnemius and soleus muscles are being stretched.

The apparatus may include a pocket for retaining the cooling means in a fixed position. The apparatus may also include a flat surface adjacent the ramp surface and means engageable with the flat surface for providing localized pressure to at least one portion of the plantar fascia. The means engageable with the flat surface may also be engageable with the ramp surface to provide localized pressure beneath the toes of the foot. The means engageable with the flat surface may comprise a dowel that is rollable along the flat surface.

In another aspect, a use of the apparatus detailed herein is disclosed for treating inflammatory symptoms associated with plantar fasciitis in a foot. In yet another aspect, a kit for treating inflammatory symptoms associated with plantar fasciitis in a foot is disclosed. The kit includes an apparatus as detailed herein and instructions for use of such apparatus.

Further aspects and advantages of the present invention will become apparent upon considering the following drawings, description, and claims.

BRIEF DESCRIPTION OF THE FIGURES

In representative photographs which illustrate non-limiting embodiments of the invention.

DETAILED DESCRIPTION

The invention will be more fully illustrated by the following detailed description of non-limiting, specific embodiments in conjunction with the aforementioned figures.

Figure 1:
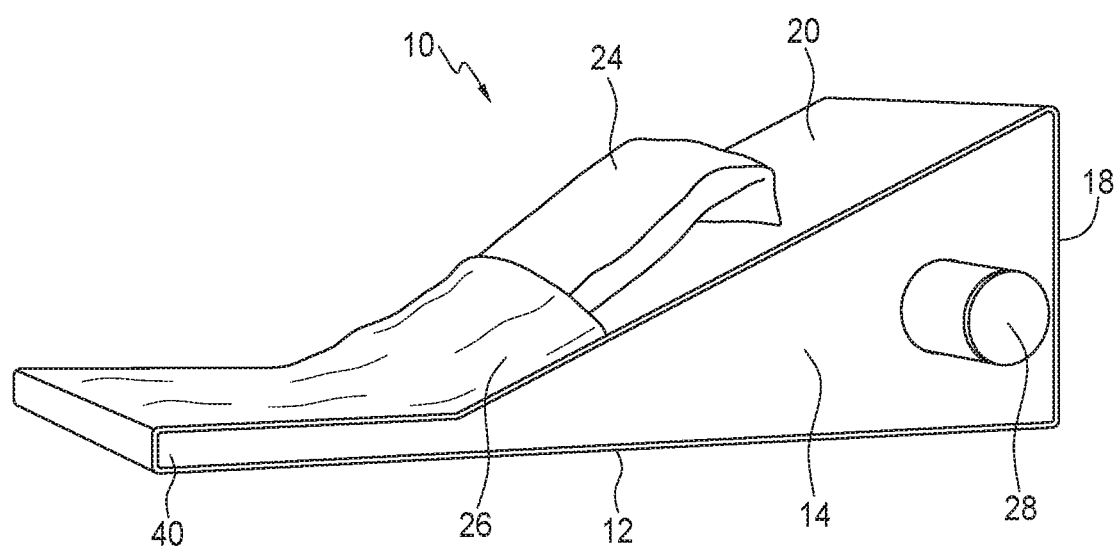
FIG. 1 is a perspective view of an apparatus for treating inflammatory symptoms associated with plantar fasciitis in a foot, according to a first embodiment of the invention.

Referring first to FIG. 1 herein, an apparatus 10 is disclosed for treating inflammatory symptoms associates with plantar fasciitis in a foot. The apparatus 10 has a base 12, two spaced-apart sides 14 and 16 (not shown), respectively, and an upstanding portion 18 that, in totality, define the apparatus 10. The apparatus 10 has an inclined ramp surface 20, as shown, for example, in FIG. 1. The apparatus 10 also has a flat surface 40, adjacent the ramp surface 20, as shown in FIG. 1.

As utilized herein, the term "plantar fasciitis" also includes the related medical condition known as plantar fasciosis.

As utilized herein the term "inflammatory symptoms" includes acute and chronic inflammatory symptoms, such as acute and chronic inflammation. The inflammatory symptoms are associated directly or indirectly with the condition commonly referred to as plantar fasciitis. Inflammatory symptoms also include tendonitis and tendonosis in the foot.

Figure 4:
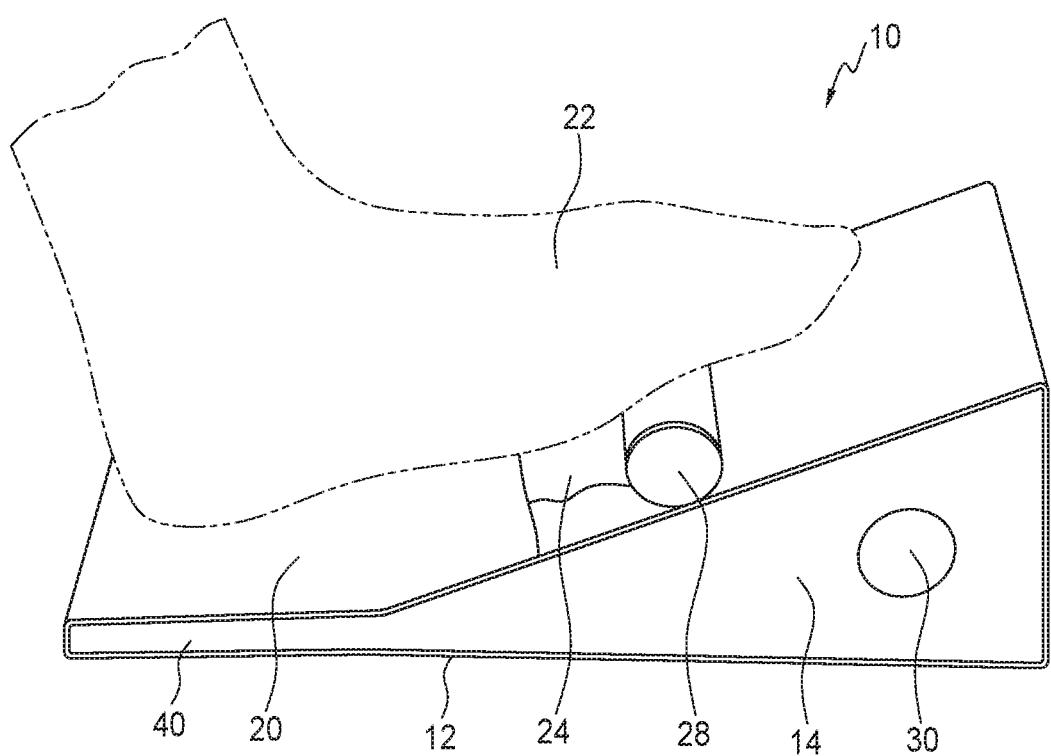
FIG. 4 is a perspective view of the apparatus of FIG. 1 demonstrating a foot being placed on the apparatus to stretch the gastrocnemius and soleus muscles, as described herein.

The apparatus 10 is optionally produced from a solid foam construction but it can be made up of other materials, such as molded plastic and the like, so long as it can withstand reasonable downward pressure from a foot 22, as shown, for example in FIG. 4 herein, and preferably so long as there is some padded heel cushion for comfort. Preferably, the apparatus 10 is produced from ethylene vinyl acetate and is a "closed cell" foam so that it can be cleaned without absorbing moisture. Additionally, the apparatus 10 is preferably formed from a constructive material so that it is lightweight and non-latex due to the prevalence of latex allergies in the population.

The inclined ramp surface 20 can be of varied degrees of inclination (with reference being made to the flat surface 40), depending on the degree of stretching required of the foot-associated gastrocnemius and soleus muscles. Preferably, the inclined ramp surface 20 is between 10 degrees and 45 degrees. More preferably, the inclined ramp surface is between 15 degrees and 30 degrees. It will be appreciated by those persons skilled in the art to which this specification relates, that the degree of inclination shown in the accompanying Figures is a non-limiting embodiment.

Figure 2:
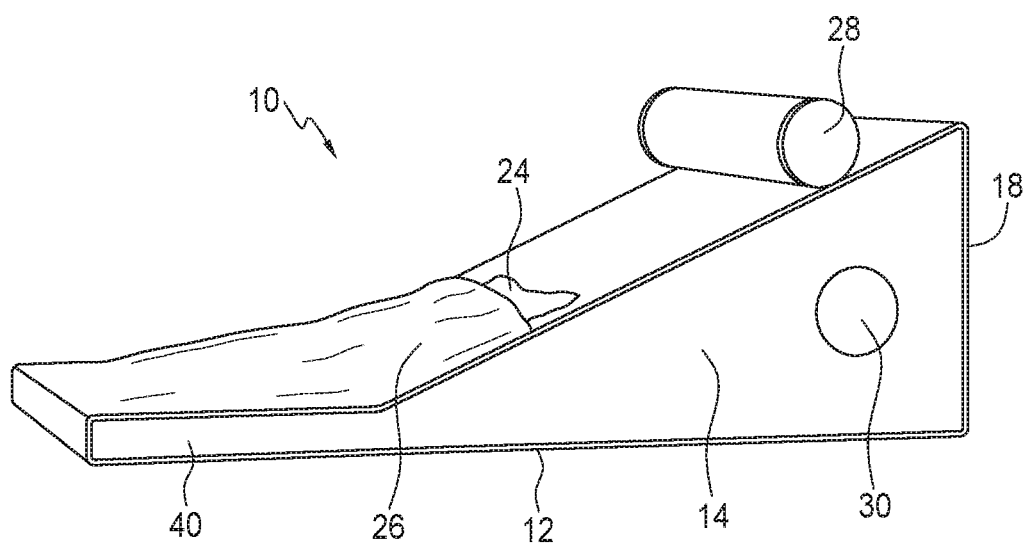
FIG. 2 is a perspective view of the apparatus of FIG. 1 detailing a dowel that engages the ramp surface of the apparatus.
Figure 3:
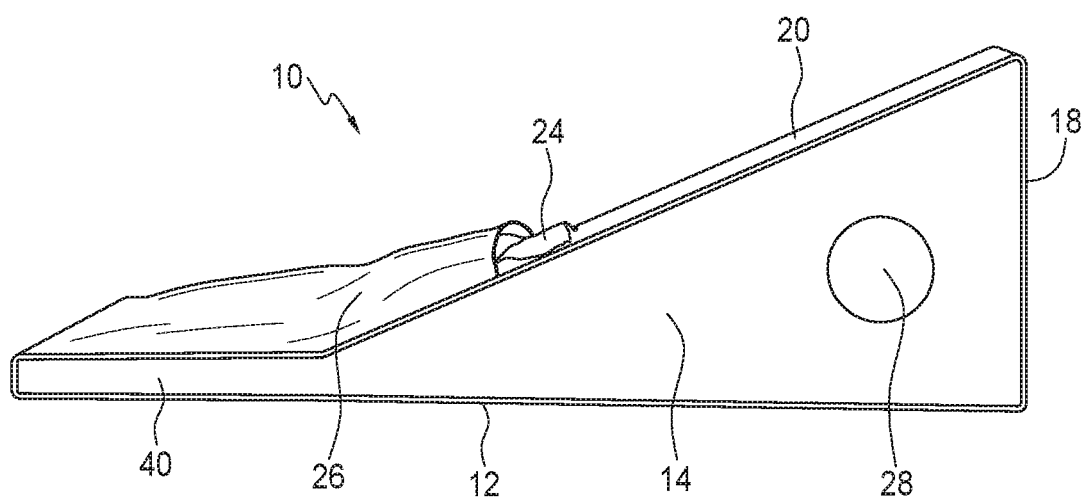
FIG. 3 is a side elevational view of the apparatus of FIG. 1 detailing the dowel in a storage position.

The apparatus 10 also includes cooling means 24 that is engageable with the inclined ramp surface 20 for cooling at least one portion of the sole of the foot 22, for example the heel portion, while the foot 22 is being stretched. The cooling means 24 may include, but is not limited to, commercially available ice packs or gel packs. Preferably, the cooling means 24 is retained in a fixed position within a pocket 26 that is incorporated into the inclined ramp surface 20. This is shown, for example, in FIG. 1 where the cooling means 24 is partially exposed from the pocket 26. However, as shown in FIGS. 2-4, in operation, the cooling means 24 is preferably maintained in a non-exposed position within the pocket 26. In an alternative embodiment, a heat pack can be utilized instead of cooling means if increased circulation and/or tissue relaxation is preferred. It is specifically contemplated that variants of the pocket 26 and its interaction with the cooling means 24 or the heat pack could be introduced into the apparatus 10.

The apparatus 10 preferably contains means 28 that are engageable with the flat surface 40 for providing localized pressure to at least one portion of the plantar fascia. In addition to the flat surface 28, the means 28 can engage with the surface of a floor (not shown) adjacent the inclined ramp surfaces 20. The means 28 are also engageable with the inclined ramp surface 20 for providing localized pressure to a portion of the foot 22 beneath the toes. When pressure is applied to this region of the foot, dorsiflexion of the toes (i.e., upward flexing) can be accomplished. The means 28 may be in the form of a dowel and can be formed of wood or other hard materials, such as formed plastic or cork. In an alternative embodiment, the means 28 may have beveled edges which are preferable for carrying out cross-friction massage on the plantar fascia. In a non-limiting, alternative embodiment, the means 28 may have be hour-glass shaped.

As shown, for example, in FIG. 2 herein, the apparatus 10 optionally contains a hole 30 initiating from one of the sidewalls 12 or 14 of the apparatus 10 for storing the means 28. Preferably the hole 30 is of a similar shape to the means 28 so as to maintain the means 28 in a tight, though accessible, storage position.

In operation, and as shown generally in FIG. 4, the sole of a foot 22 is placed on the inclined ramp surface 22 of the apparatus 10. This position allows for suitable stretching of the foot-associated gastrocnemius and soleus muscles (not shown). A portion of the sole of the foot 22 is cooled by engaging the cooling means 24. Because plantar fasciitis often afflicts the heel portion of the foot 22, the cooling means 24 preferably is positioned to engage the heel portion of the foot 22 when utilizing this apparatus 10. Preferably the stretching and cooling steps disclosed herein occur simultaneously. As previously noted, a heat pack can be utilized instead of cooling means if increased circulation and/or tissue relaxation is a preferred outcome.

Additionally, localized pressure can be applied to at least one portion of the plantar fascia of the foot 22 by rocking the foot over the means 28, preferably when the means 28 engages the flat surface 40 (not shown). Additionally, localized pressure can be applied to a portion of the foot 22 beneath the toes by rocking this portion of the foot 22 over the means. When pressure is applied to this region of the foot, dorsiflexion of the toes (i.e., upward flexing) can be accomplished. A dowel-like shape is preferable for allowing this pressure to be localized. As noted above, the dowel-like shape may have beveled edges which are preferable for carrying out cross-friction massage on the plantar fascia.

Preferably, the stretching, cooling, and localized pressure steps disclosed herein occur simultaneously or nearly simultaneously. In addition, the apparatus 10 detailed herein can be packaged as a kit (not specifically shown) for treating inflammatory symptoms associated with plantar fasciitis in a foot. In addition to the apparatus 10, or similar embodiments thereof, the kit would also include instructions for the use thereof. The apparatus 10 can also be used to treat hypertonicity of the muscles in the foot.

Example 1. Treating Inflammatory Symptoms Associated with Plantar Fasciitis in a Foot NS, a female individual suffering from inflammatory symptoms associated with plantar fasciitis in her foot, utilized the apparatus 10 detailed herein as follows. Specifically using the apparatus 10, NS cooled the heel of her foot, and stretched her gastrocnemius and soleus muscles, fascia and toes for 5 minutes at a time, on an hourly basis during the day, both at home while standing at a counter and at work while sitting at her desk or standing in her office. NS reported immediate pain relief from the inflammatory symptoms associated with plantar fasciitis in her foot after each therapeutic session. Full recovery from the inflammatory symptoms associated with plantar fasciitis in her foot were achieved within approximately two (2) weeks.

Additionally, NS continues to maintain good foot health by using the apparatus described herein on both of her feet twice daily (for a period of 5-10 minutes per session) to prevent future onset of plantar fasciitis. Accordingly, the apparatus and method described herein can be used not only to treat inflammatory symptoms associated with plantar fasciitis, but they can also be used to help prevent the onset of the condition.

Example 2. Treating Inflammatory Symptoms Associated with Plantar Fasciitis in a Foot JD, a 51 year-old female, was instructed by her Chiropractor to use the device 10 immediately after being diagnosed with plantar fasciitis. She utilized the apparatus 8-10 times throughout the day, both at home and at work, to cool the heel of her foot and stretch her gastrocnemius and soles muscles, fascia and toes. She held each stretch for approximately 30 seconds to approximately one minute with the exception of use of the cooling means 24, which was used for 2-3 minutes at a time to relieve pain and swelling, and other associated inflammatory symptoms. JD reported that after three weeks of the above-mentioned treatment, her pain was relieved by approximately 90% and her mobility increased by approximately same.

Thus, it will be seen from the foregoing embodiments and description that there has been described a method of treating inflammatory symptoms associated with plantar fasciitis in a foot using an apparatus substantially as described herein.

While specific embodiments of the invention have been described and illustrated, such embodiments should be considered illustrative of the invention only and not as limiting the invention as construed in accordance with the accompanying claims. It will be understood by those skilled in the art that various changes, modifications and substitutions can be made to the foregoing embodiments without departing from the principle and scope of the invention expressed in the claims made herein.

What is claimed is:

1. An apparatus for treating inflammatory symptoms associated with plantar fasciitis in a foot, the apparatus comprising:
   an inclined ramp surface;
   a flat surface adjacent to the inclined ramp surface;
   a dowel rollable along both the inclined ramp surface and the flat surface; and
   a pocket coupled to the flat surface, wherein the pocket is disposed radially outward from the flat surface and ascending the inclined ramp surface.

2. The apparatus of claim 1, further comprising a gel pack retained in the pocket.

3. The apparatus of claim 2, wherein the gel pack is configured for cooling a portion or all of a sole of the foot.

4. The apparatus of claim 2, wherein the pocket is configured to retain at least a portion of the gel pack in a fixed position.

5. The apparatus of claim 1, further comprising a hole in a sidewall of the apparatus for storing the dowel.

6. The apparatus of claim 1, wherein the dowel is engageable with both the inclined ramp surface and the flat surface adjacent to the inclined ramp surface for providing localized pressure to a portion or all of the foot.

7. The apparatus of claim 1, wherein the inclined ramp surface is configured for stretching a gastrocnemius muscle and a soleus muscle associated with the foot.

8. The apparatus of claim 1, wherein the pocket is coupled to the inclined ramp surface.

9. The apparatus of claim 1, wherein the apparatus comprises a solid foam material.

10. The apparatus of claim 9, wherein the solid foam material is configured to withstand downward pressure from the foot.

11. The apparatus of claim 1, wherein the inclined ramp surface has a degree of inclination with reference to the flat surface, wherein the degree of inclination is between 10 degrees and 45 degrees.

12. A kit for treating inflammatory symptoms associated with plantar fasciitis in a foot, the kit comprising:
   the apparatus of claim 1; and
   instructions for use.

* * * * *